(12) United States Patent
Booch et al.

(10) Patent No.: US 8,936,154 B2
(45) Date of Patent: Jan. 20, 2015

(54) DIAPER PACKAGE SUITABLE AS A CHANGING MAT

(75) Inventors: Thorsten Booch, Euskirchen (DE); Andreas Peter Motsch, Schwalbach am Taunus (DE); Fernando Bayod, Strombeek-Bever (BE)

(73) Assignee: The Procter & Gamble Company, Cincinnati, OH (US)

( * ) Notice: Subject to any disclaimer, the term of this patent is extended or adjusted under 35 U.S.C. 154(b) by 379 days.

(21) Appl. No.: 13/537,751

(22) Filed: Jun. 29, 2012

(65) Prior Publication Data

US 2013/0001108 A1    Jan. 3, 2013

(30) Foreign Application Priority Data

Jun. 30, 2011  (EP) .................................. 11005376

(51) Int. Cl.
| | | |
|---|---|---|
| *B65D 85/16* | (2006.01) | |
| *B65D 71/06* | (2006.01) | |
| *A61F 13/551* | (2006.01) | |
| *B65D 81/36* | (2006.01) | |

(52) U.S. Cl.
CPC ............ *A61F 13/5511* (2013.01); *B65D 85/16* (2013.01); *B65D 71/063* (2013.01); *B65D 81/36* (2013.01)
USPC .......................................... 206/494; 206/440

(58) Field of Classification Search
CPC ...... B65D 85/16; B65D 81/36; B65D 71/063; A61F 13/55105; A61F 13/5511
USPC .......... 206/38, 83.5, 233, 434, 438, 440, 442, 206/451, 494, 581; 53/461, 492; 229/87.01
See application file for complete search history.

(56) References Cited

U.S. PATENT DOCUMENTS

| | | | | |
|---|---|---|---|---|
| 4,555,017 A | * | 11/1985 | Blackmore | 206/83.5 |
| 5,062,557 A | * | 11/1991 | Mahvi et al. | 224/153 |
| 5,259,550 A | | 11/1993 | Kuchenbecker | |
| 5,350,063 A | * | 9/1994 | Berdan, II | 206/442 |
| 5,443,161 A | * | 8/1995 | Jonese | 206/581 |
| 5,934,470 A | | 8/1999 | Bauer et al. | |
| 6,168,022 B1 | * | 1/2001 | Ward et al. | 206/581 |
| 6,298,993 B1 | * | 10/2001 | Kalozdi | 206/581 |
| 7,204,368 B2 | | 4/2007 | Cheaure et al. | |
| 7,262,335 B2 | | 8/2007 | Motsch et al. | |
| 7,370,760 B2 | | 5/2008 | Clough | |
| 7,487,873 B2 | * | 2/2009 | Larsson et al. | 206/494 |
| 2007/0233032 A1 | * | 10/2007 | Rau | 206/438 |
| 2008/0142380 A1 | * | 6/2008 | Unruh et al. | 206/170 |
| 2010/0163609 A1 | | 7/2010 | Bull | |
| 2010/0243504 A1 | * | 9/2010 | Long et al. | 206/494 |

FOREIGN PATENT DOCUMENTS

| | | |
|---|---|---|
| EP | 0 468 860 A1 | 1/1992 |
| EP | 0 413 122 B1 | 2/1993 |
| EP | 0 942 881 A1 | 9/1999 |

OTHER PUBLICATIONS

EP International Search Report dated Sep. 21, 2011 (6 pages).
PCT International Search Report mailed Nov. 23, 2012 (8 pages).
EP International Search Report, dated Oct. 14, 2011 (5 pages).

* cited by examiner

*Primary Examiner* — Luan K Bui
(74) *Attorney, Agent, or Firm* — William E. Gallagher; Richard L. Alexander

(57) ABSTRACT

A package for disposable diapers having a portion of the package usable as a baby changing mat.

14 Claims, 4 Drawing Sheets

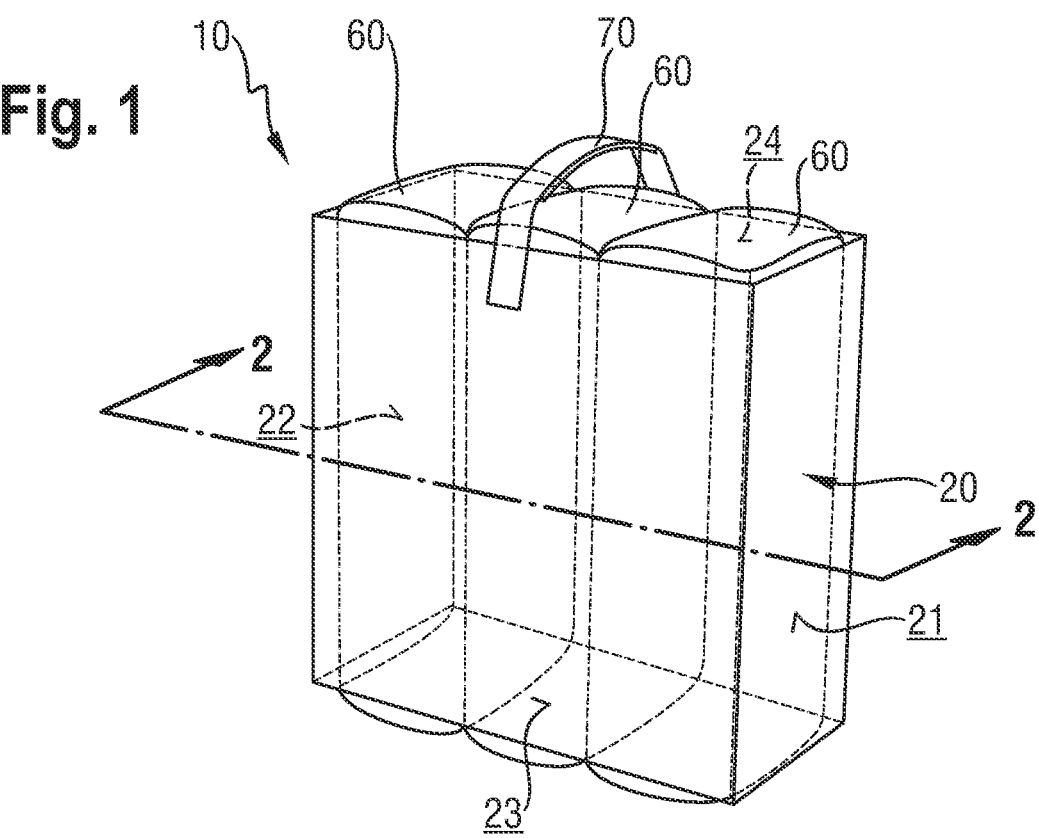

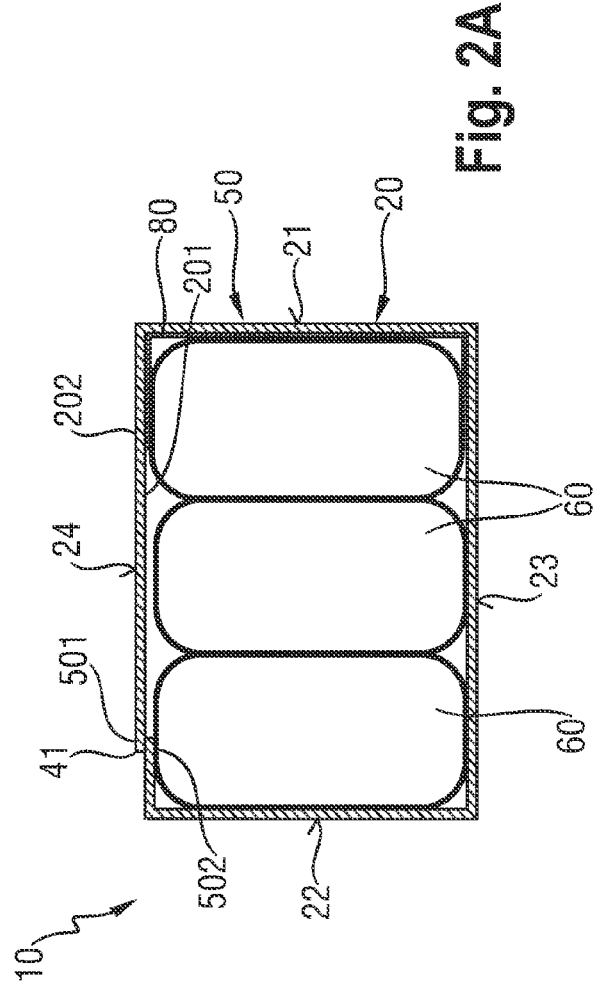
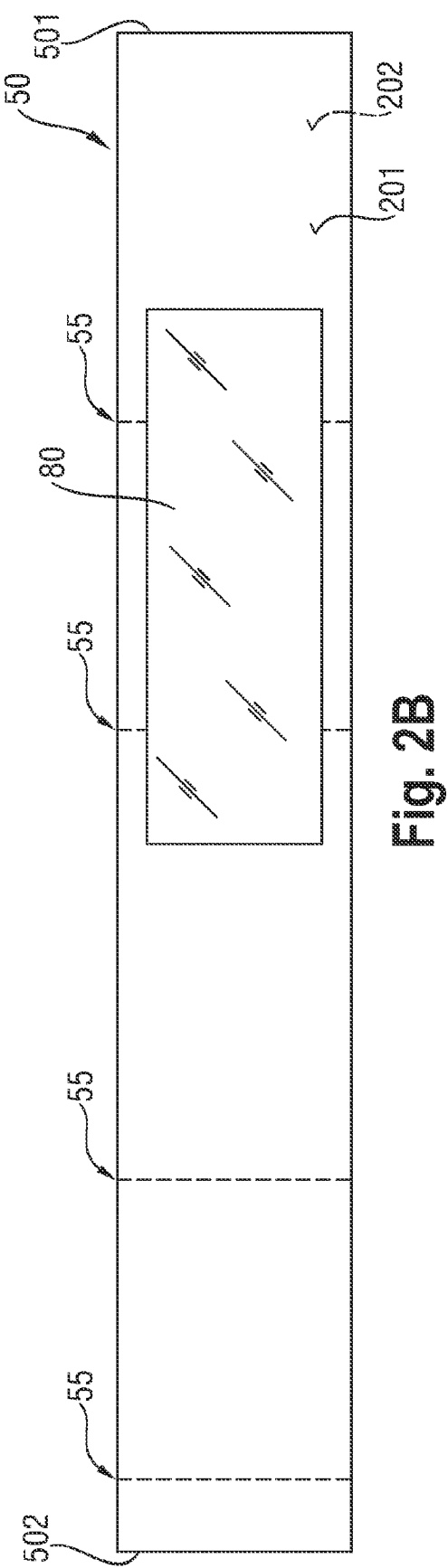

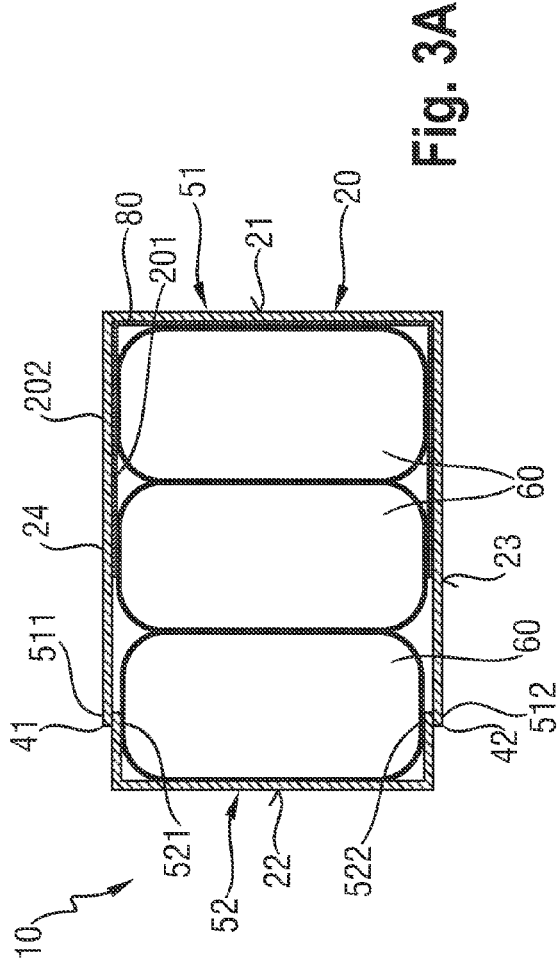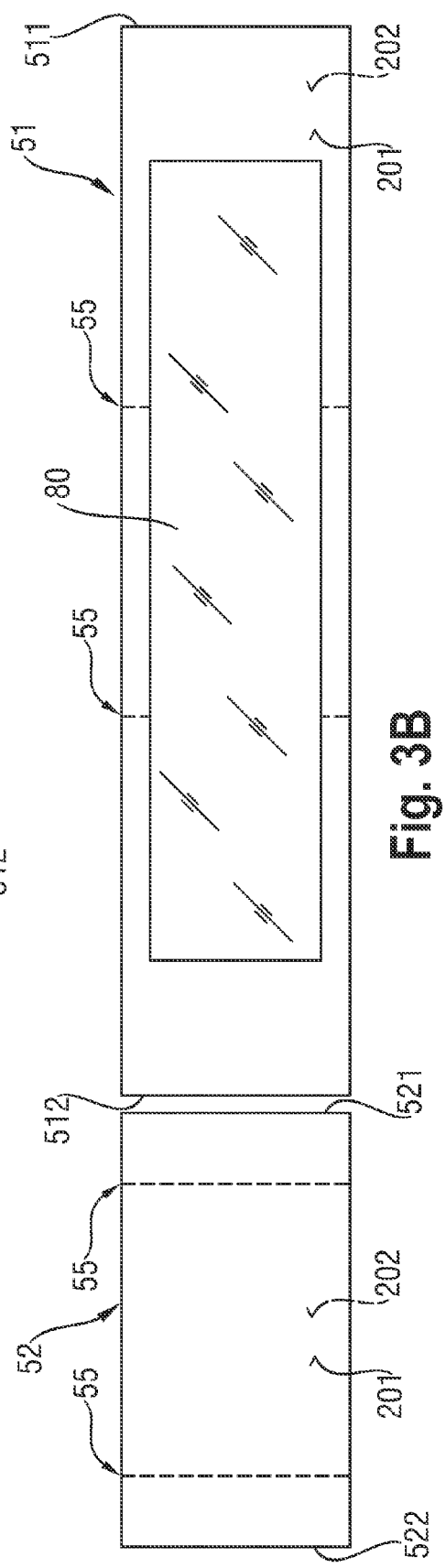

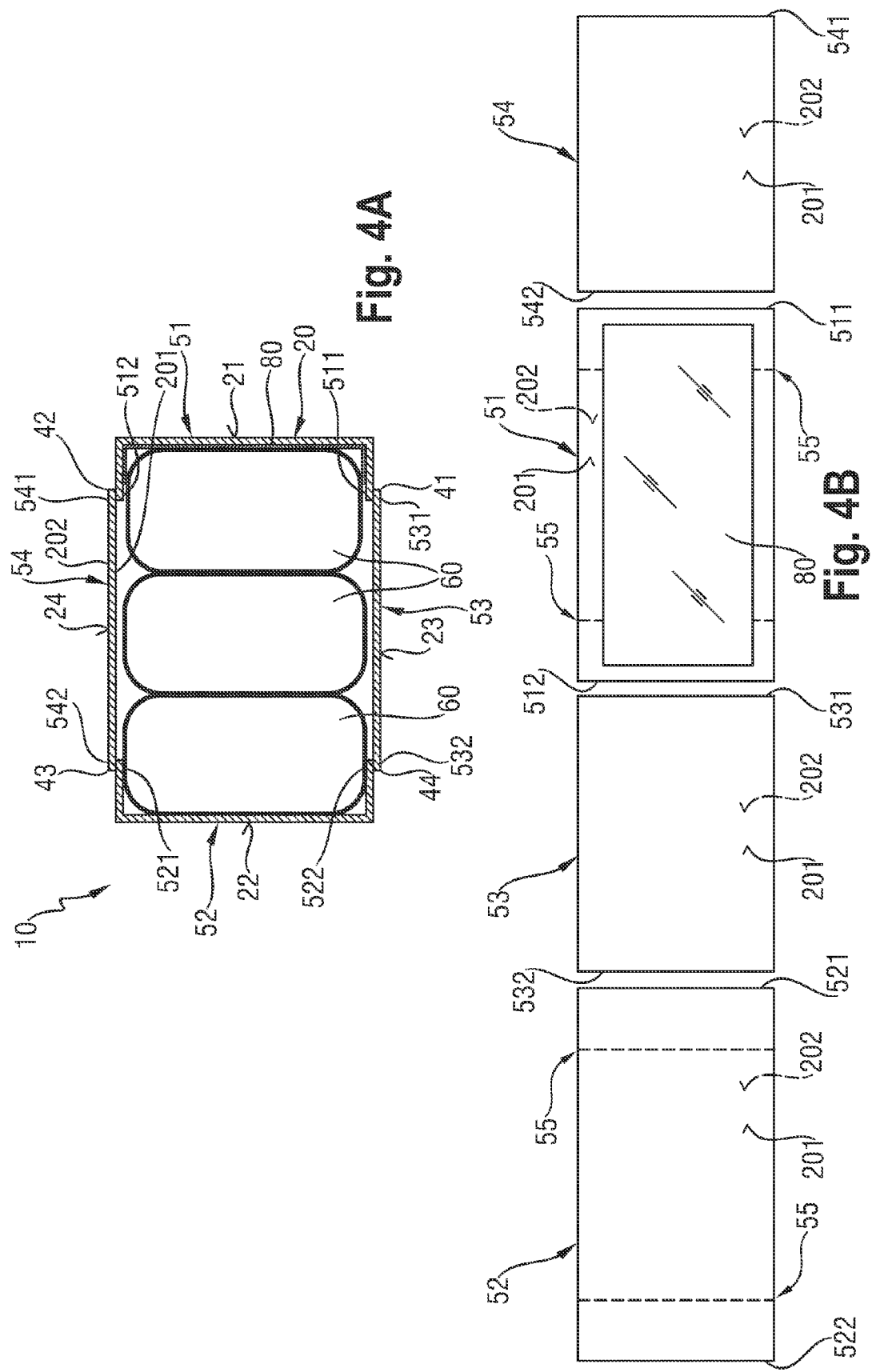

DIAPER PACKAGE SUITABLE AS A CHANGING MAT

CROSS REFERENCE TO RELATED APPLICATION

This application claims priority to European Patent Application No. EP 11005376.6, filed Jun. 30, 2011.

FIELD OF THE INVENTION

The present invention is directed to packages for disposable diapers having a portion of the package usable as a baby changing mat.

BACKGROUND OF THE INVENTION

Changing mats are typically used by caregivers in order to apply disposable diapers to a baby while the baby is lying on the changing mat. Changing mats which are currently on the market are typically made from foam padding covered in a PVC layer.

The problem with such changing mats is that they may be quite space consuming since the material of which they are made may not be easily folded due to a certain resiliency of the material. This may be a substantial disadvantage especially when people are travelling since the place available for the belongings, for example in the car may be limited. Furthermore, people may sometimes even forget to bring the changing mat with them and therefore need to buy a new one. This is not cost-effective.

Therefore, there is a need for a simple changing mat that a caregiver may easily have at hand and which may be produced in a cost-effective manner.

BRIEF DESCRIPTION OF THE DRAWINGS

FIG. 1 is a perspective view of a package according to an embodiment of the present invention.

FIG. 2A is a cross-sectional view of the package of FIG. 1 taken at the section line 2-2 comprising a wrap-around material 20 made of a single piece of material 50 according to an embodiment of the present invention.

FIG. 2B is a plan view of the wrap around comprised by the package of FIG. 2A.

FIG. 3A is a cross-sectional view of the package of FIG. 1 taken at the section line 2-2 comprising a wrap-around material 20 made of two pieces of material 51 and 52 according to an embodiment of the present invention.

FIG. 3B is a plan view of the wrap around comprised by the package of FIG. 3A.

FIG. 4A is a cross-sectional view of the package of FIG. 1 taken at the section line 2-2 comprising a wrap-around material 20 made of four pieces of material 51, 52, 53, 54 according to an embodiment of the present invention.

FIG. 4B is a plan view of the wrap around comprised by the package of FIG. 4A.

DETAILED DESCRIPTION OF THE INVENTION

"Changing mat" is used herein to refer to refer to an element which is laid on a stable surface such a table in order to lay down a baby on it in order to change the baby's diaper.

"Tissue sheet(s)" is used herein to refer to sheet(s) which is/are formed by a wet-laid or air-laid paper-making process.

"Attached" is used herein to refer to configurations whereby a first element is directly secured to another element by affixing the first element directly to a second element or whereby a first element is indirectly secured to a second element by affixing the first element to a third, intermediate member, which in turn is affixed to the second element.

"Interior surface" is used herein to refer to the surface of a wrap-around material or a side panel which is facing towards the disposable diapers which are wrapped by the wrap-around material.

"Exterior surface" is used herein to refer to the surface of the wrap-around material or a side panel thereof which is opposite to the interior surface of the wrap-around material and facing away from the disposable diapers which are wrapped by the wrap-around material.

A package 10 according to the present invention comprises disposable diapers 60 being wrapped by a wrap-around 20 having an interior and an exterior surface 201, 202 wherein one or more substrate(s) 80 is/are attached to at least a portion of the interior surface of the wrap-around 201 as shown for example in FIGS. 2, 3 and 4. The substrate(s) may be woven sheet(s), nonwoven sheet(s), knitted sheet(s) and/or tissue sheet(s). At least a portion of the wrap-around in combination with at least a portion of the substrate(s) is suitable for use as a changing mat.

Such a changing mat is particularly advantageous from a sustainability point of view since the same material, i.e. the wrap-around may be used in order to pack the disposable diapers and in order to change a baby. Furthermore, the consumer who is buying diapers will always have a changing mat available since it is part of the package. In addition, nonwoven webs and tissue sheets may be produced in a cost-effective manner which means that the changing mat may also be produced in a cost-effective manner.

The Wrap-Around

The wrap-around 20 may comprise a first and a second opposing side panel 21, 22 which are parallel to each other and a third and a fourth side panel 23, 24 which are parallel to each other as shown for example in FIGS. 1 to 4.

Each of the first and the second side panels 21, 22 may be perpendicular to each of the third and fourth side panels 23, 24 as for example shown in FIGS. 1 to 4. In such embodiments, the package 10 typically has a parallelepiped shape.

The first and the second side panels 21, 22 may have any shape. They may for example have a rectangular shape as for example shown in FIG. 1.

The size of the area of the interior surface of the wrap-around 201 which is covered by the substrate(s) may be of at least 50%, or at least 80%, or of 50% to 90% of the size of the interior surface of the wrap-around 201.

A film may be laminated to at least one of the substrate(s) 80 and facing towards the interior surface of the wrap-around 201. The film may be laminated to at least one of the substrates by the application of heat and/or pressure. The film may also be adhesively laminated. The film may be a polyethylene or a polypropylene film. This is particularly advantageous since the substrate(s) 80 may absorb body exudates that may leak out of the diaper whereas the film may reduce the risk that body exudates come into contact with the interior surface of the wrap-around 201 and therefore wet and soil it.

The attachment means that may be used in order to attach the substrate(s) 80 to the interior surface of the wrap-around 201 include adhesive bonds, heat bonds, pressure bonds, ultrasonic bonds, dynamic mechanical bonds, or any other suitable attachment means or combinations of these attachment means which are known in the art.

The wrap-around 20 may comprise or consist of cardboard material, corrugated board material and/or polymeric material.

The wrap-around 20 may be made of a single piece of material or of two or more pieces of material which are attached to each other. In any of these embodiments, the wrap-around may comprise one or more frangible line(s) of weakness or may be closed with one or more adhesive tapes in order to make easier the opening of the package 10 by the caregiver. The interior surface of the wrap-around 201 may not comprise any of the substrate(s) 80 which are attached to it in the area(s) wherein the frangible line(s) of weakness is/are present in order to make easier the tearing of the wrap-around along then frangible line(s) of weakness and not tear the substrate(s) inadvertently.

The wrap-around 20 may comprise two frangible line(s) of weakness. In such embodiments, only a portion of the wrap-around 20, namely the portion of the wrap-around 20 which is delimited by the two frangible line(s) in combination with at least a portion of the substrate(s) 80 may be used as a changing mat. Hence, the substrate(s) 80 may be only present in the portion of the wrap-around 20 which is delimited by the two frangible line(s). This is particularly advantageous since only this portion of the interior surface of the wrap-around 201 needs to comprise the substrate(s) 80. This may reduce the manufacturing costs for such of the package 10 and therefore of the changing mat.

As used herein the term "attachment zone" refers to the overlap between the two opposing edges of a single piece of material which are attached to each other in order to form the wrap-around 20 in the embodiment wherein the wrap-around 20 is made of a single piece of material. The term "attachment zone" refers to the overlap between the edges of two different pieces of material which are attached to each other in order to form a portion of the wrap-around 20 in the embodiments wherein the wrap-around 20 is made of two or more pieces of material.

The wrap-around 20 may be made of a single piece of material or of two or more pieces of material which are attached to each other. In the embodiments, wherein the wrap-around 20 is made of two or more pieces of material, the substrate(s) 80 may be comprised by all the different pieces of material the wrap-around 20 is made of or by only some of them.

Embodiments Wherein the Wrap-Around 20 is Made of One Piece of Material

In some embodiments, the wrap-around material 20 is made of a single piece of material 50, as for example shown in FIGS. 2A and 2B.

In such embodiments, the different side panels 21, 22, 23, 24 of the wrap-around material 20 are made by folding the single piece of material 50 along folding lines 55. Such folding lines 55 are typically parallel to each other.

In such embodiments, as for example shown in FIGS. 2A and 2B, the single piece of material 50 comprises a pair of opposing edges 501, 502 wherein the opposing edges 501, 502 of the single piece of material 50 are attached to each other along an attachment zone 41 in order to form the wrap-around material 20 as for example shown in FIG. 2A.

The wrap-around 20 can be easily opened by the caregiver by detaching the two opposing edges 501, 502 along the attachment zone 41 in order to use it as a changing mat.

Embodiments Wherein the Wrap-Around 20 is Made of Two Pieces of Material

In some embodiments, the wrap-around material 20 is made of two pieces of material 51, 52 as for example shown in FIGS. 3A and 3B.

In such embodiments, the different side panels of the wrap-around material 21, 22, 23, 24 are made by folding each of the first and second pieces of material 51, 52 along folding lines 55. Such folding lines 55 are typically parallel to each other.

In such embodiments, as for example shown in FIGS. 3A and 3B, the first and second pieces of material 51, 52 comprising each a pair of first and second opposing edges 511, 512, 521, 522 wherein the first edge 511 of the first piece of material 51 is attached to the first edge 521 of the second piece of material 52 along a first attachment zone 41 and wherein the second edge 512 of the first piece of material 51 is attached to the second edge 522 of the second piece of material 52 along a second attachment zone 42.

The wrap-around can be easily opened by the caregiver by detaching the first piece 51 of material from the second piece of material 52 along any of the first or second attachment zone 41, 42 in order to use the wrap-around as a changing mat.

The caregiver may even detach the first piece of material 51 from the second piece of material 52 along both first and second attachment zones 41, 42 in order to only use one of the two pieces 51, 52 as a changing mat.

Embodiments Wherein the Wrap-Around Material is Made of Four Pieces of Material

In some other embodiments, the wrap-around material 20 is made of four pieces of material 51, 52, 53, 54 as for example shown in FIGS. 4A and 4B.

In such embodiments, the different side panels of the wrap-around material 21, 22, 23, 24 are made by folding each of the first and second pieces of material 51, 52 along folding lines 55 which correspond to the connecting edges of the different panels of the wrap-around material 20. Such folding lines 55 are typically parallel to each other.

In such embodiments, as for example shown in FIGS. 4A and 4B, the first, second, third and fourth piece of material 51, 52, 53, 54 comprising each a pair of first and second opposing edges 511, 512, 521, 522, 531, 532, 541, 542. The first edge of the first piece of material 511 is attached to the first edge of the third piece of material 531 along a first attachment zone 41, the second edge of the first piece of material 512 is attached to the first edges of the fourth piece of material 541 along a second attachment zone 42, the first edge of the second piece of material 521 is attached to the second edge of the fourth piece of material 542 along a third attachment zone 43 and the second edge of the second piece of material 522 is attached to the second edge of the third piece of material 532 along a fourth attachment zone 44

The wrap-around 20 can be easily opened by the caregiver by detaching any of the pieces of material 51, 52, 53, 54 of the wrap-around 20 from the contiguous piece of material it is attached to in order to use the wrap-around 20 as a changing mat.

The caregiver may even only use one, two or three of the pieces of materials as a changing mat by detaching them from the rest of the wrap-around 20.

The wrap-around 20 may also be made of 3 pieces of material or more than 4 pieces of material. In all these embodiments, the caregiver may also choose to use the whole wrap-around 20 as a changing mat or only some of the pieces the wrap-around 20 is made of.

The Attachment Zones

In some embodiments, as for example shown in FIGS. 2A, 3A, 4A, the attachment zones 41, 42, 43, 44 have an interior-to-exterior configuration which means that a portion of the interior surface of the wrap-around material 201 is attached to a portion of the exterior surface of the wrap-around material 202 in order to form the attachment zones 41, 42, 43, 44.

In some other embodiments at least one of the attachment zones 41, 42, 43, 44 has an interior-to-interior configuration which means that a portion of the interior surface of the wrap-around material 201 is attached to another portion of the interior surface of the wrap-around material 201 in order to form the attachment zone 41, 42, 43, 44.

The attachment means that may be used in order to attach a piece of material to itself or a piece of material to another piece of material in order to form an attachment zone 41, 42, 43, 44 include adhesive bonds, heat bonds, pressure bonds, ultrasonic bonds, dynamic mechanical bonds, or any other suitable attachment means or combinations of these attachment means which are known in the art.

The Substrate(s)

The woven sheet(s), nonwoven sheet(s) and knitted sheet(s) may be made from synthetic fibers, cellulose fibers, wool fibers and/or silk fibers or combinations thereof. The cellulose fibers may be cotton fibers or pulp fibers.

The nonwoven sheets) may be formed by a carding process, or a spunbond process or a meltblown process. The nonwoven sheet(s) may have a basis weight of 10 gsm to 400 gsm, or 20 gsm to 300 gsm or 50 gsm to 200 gsm.

Two or more substrates (80) may be attached to at least a portion of the interior surface of the wrap-around (201). In such embodiments, the two or more substrates 80 may overlay and be attached to each other. An overlying substrate may be attached to 5 to 30% or 5 to 20% of the surface of the directly underlying substrate. The substrates 80 may be thermally bonded to each other. They may also be attached to each other by using a peelable adhesive or a pressure sensitive adhesive in order to be able to separate them without damaging them.

A lotion may be applied to any of the substrate(s) 80 in order to reduce the risk of skin rash due to the contact of the skin of the baby with the substrate(s). The lotion may comprise emollient(s), immobilizing agent(s), surfactant(s) and/or buffering agent(s). An emollient, as used herein, is a material that softens, soothes, supples, coats, lubricates, moisturizes or cleanses the skin. An immobilizing agent, as used herein, is a material that helps in stabilizing the composition on the substrate and limiting its transfer to the skin. The lotion may also comprise optional ingredients including solvents, diluents, viscosity modifiers, perfumes, antibacterial actives, pharmaceutical actives, film formers, deodorants, opacifiers, pigments, dyes, and coloring agents, astringents, solvents and the like.

The Disposable Diapers

The disposable diapers 60 may be comprised in one or more flexible packages of absorbent articles, such as from 1 to 5 flexible packages, for example 1, 2, 3, 4 or 5 as for example shown in FIGS. 1 to 4. The flexible packages may be of the same size or of different sizes. Suitable flexible packages are for example described in WO2009/129202.

In some embodiments, wherein at least a portion of the interior surface of the wrap-around does not comprise any of the substrate(s) such a portion may comprise a coating or one or more adhesive tapes or a releasable adhesive in order to increase the friction force that is exerted by each of the flexible packages onto the wrap-around 20. In such embodiments, only discrete areas of the portion of the interior surface of the wrap-around 201 which does not comprise any of the substrate(s) 80 may be coated in order to increase the friction force that is exerted by each of the flexible packages onto the wrap-around 20. The coating may for example be in the form of a dot or a stripe pattern.

These embodiments are particularly advantageous since they provide a good immobilization of the flexible packages inside the package 10 and therefore reduce the risk that one of the flexible packages slides from the package 10.

In some other embodiments, the package 10 is wrapped either partially or completely in a plastic film or a plastic bag. The plastic film may be a shrink film or a stretch film or two sleeves of plastic film which are attached to each other.

The package may comprise a handle 70 as for example shown in FIG. 1.

What is claimed is:

1. A package comprising disposable diapers being wrapped by a wrap-around having an interior and an exterior surface wherein one or more substrate(s) is/are attached to at least a portion of the interior surface of the wrap-around, wherein the substrate(s) is/are selected from the group consisting of woven sheets, nonwoven sheets, knitted sheets, tissue sheets and any combination thereof, at least a portion of the wrap-around in combination with at least a portion of the substrate(s) being suitable for use as a changing mat.

2. The package according to claim 1 wherein the wrap-around comprises:
   i) a first and a second opposing side panel being parallel to each other; and
   ii) a third and a fourth side panel being parallel to each other.

3. The package according to claim 1 wherein the size of the area of the interior surface of the wrap-around which is covered by the substrate(s) is of at least 50% of the size of the interior surface of the wrap-around.

4. The package according to claim 1 wherein the wrap-around is made of a single piece of material comprising a pair of opposing edges wherein the opposing edges of the single piece of material are attached to each other along an attachment zone.

5. The package according to claim 1, wherein the wrap-around is made of a first and a second piece of material comprising each a pair of first and second opposing edges wherein the first edge of the first piece of material is attached to the first edge of the second piece of material along a first attachment zone and wherein the second edge of the first piece of material is attached to the second edge of the second piece of material along a second attachment zone, and wherein the substrate(s) is/are comprised by the first and/or the second piece(s) of material.

6. The package according to claim 1, wherein the wrap-around is made of:
   a first, second, third and fourth piece of material comprising each a pair of first and second opposing edges wherein
   the first edge of the first piece of material is attached to the first edge of the third piece of material along a first attachment zone, and the second edge of the first piece of material is attached to the first edge of the fourth piece of material along a second attachment zone and the first edge of the second piece of material is attached to the second edge of the fourth piece of material along a third attachment zone; and
   the second edge of the second piece of material is attached to the second edge of the third piece of material along a fourth attachment zone; and
   wherein the substrates(s) is/are comprised by any of the pieces of material selected from the group consisting of the first piece of material, the second piece of material, the third piece of material, the fourth piece of material and any combinations thereof.

7. The package according to claim 1 wherein two or more substrate(s) are attached to at least a portion of the interior surface of the wrap-around and wherein the substrates overlay each other.

8. The package according to claim 1 wherein the woven sheet(s), nonwoven sheet(s) and knitted sheet(s) are made from fibers selected from the group consisting of synthetic fibers, cellulose fibers, wool fibers, silk fibers and any combination thereof.

9. The package according to claim 8 wherein the cellulose fibers are pulp fibers or cotton fibers.

10. The package according to claim 1, wherein each of the one or more woven sheet(s), nonwoven sheet(s) or knitted sheet(s) have a basis weight of 10 to 400 gsm.

11. The package according to claim 1 wherein a film is laminated to at least one of the substrate(s) and facing towards the interior surface of the wrap-around.

12. The package according to claim 1 wherein the wrap-around comprises a material selected from the group consisting of cardboard material, corrugated board material, polymeric material and any combinations thereof.

13. The package according to claim 1 wherein the disposable diapers are comprised in one or more flexible packages.

14. A method for changing a diaper, comprising the step of using at least a portion of the wrap-around in combination with at least a portion of the substrate(s) according to claim 1 as a changing mat.

\* \* \* \* \*